United States Patent
Alanazi et al.

(10) Patent No.: US 10,071,024 B1
(45) Date of Patent: Sep. 11, 2018

(54) WEARABLE PILLBOX REMINDER

(71) Applicants: Mohammed Alanazi, Philadelphia, PA (US); Hadel Alenezi, Philadelphia, PA (US)

(72) Inventors: Mohammed Alanazi, Philadelphia, PA (US); Hadel Alenezi, Philadelphia, PA (US)

(*) Notice: Subject to any disclaimer, the term of this patent is extended or adjusted under 35 U.S.C. 154(b) by 0 days.

(21) Appl. No.: 15/643,120

(22) Filed: Jul. 6, 2017

(51) Int. Cl.
| | |
|---|---|
| *G08B 1/00* | (2006.01) |
| *A61J 7/04* | (2006.01) |
| *G08B 5/38* | (2006.01) |
| *G08B 6/00* | (2006.01) |
| *G08B 3/10* | (2006.01) |
| *A45F 5/00* | (2006.01) |
| *A61J 1/03* | (2006.01) |
| *A61B 5/024* | (2006.01) |

(Continued)

(52) U.S. Cl.
CPC ............ *A61J 7/0418* (2015.05); *A45F 5/00* (2013.01); *A61B 5/024* (2013.01); *A61B 5/14542* (2013.01); *A61B 5/6831* (2013.01); *A61B 5/742* (2013.01); *A61B 5/7405* (2013.01); *A61B 5/746* (2013.01); *A61B 5/7455* (2013.01); *A61J 1/03* (2013.01); *G08B 3/10* (2013.01); *G08B 5/38* (2013.01); *G08B 6/00* (2013.01); *A45F 2005/008* (2013.01); *A61J 2200/50* (2013.01); *A61J 2200/74* (2013.01)

(58) Field of Classification Search
None
See application file for complete search history.

(56) References Cited

U.S. PATENT DOCUMENTS

| | | | |
|---|---|---|---|
| 4,785,981 A | 11/1988 | Rodman | |
| 5,802,014 A * | 9/1998 | Danko | A44C 5/003 224/165 |

(Continued)

FOREIGN PATENT DOCUMENTS

| | | |
|---|---|---|
| CN | 105030546 B | 6/2016 |
| CN | 105769574 A | 7/2016 |

OTHER PUBLICATIONS

Kwanwa, "Cheap Cute Pill Box in Wrist Watch Design, with 5 Daily Alarm and 24 Hour Countdown Timer Function", Wayback Machine Internet Archive, URL: https://www.alibaba.com/product-detail/Cheap-cute-pill-box-in-wrist_1400513332.html, 2 Pages total, (Aug. 28, 2015).

(Continued)

*Primary Examiner* — Thomas McCormack
(74) *Attorney, Agent, or Firm* — Oblon, McClelland, Maier & Neustadt, L.L.P.

(57) ABSTRACT

A wearable pillbox and a method are described. The pillbox includes a first compartment hingedly connected with a first cover and configured to store medicine to be consumed at a first dose time, a second compartment hingedly connected with a second cover and configured to store medicine to be consumed at a second dose time, the second compartment located adjacent to the first compartment and the second cover configured to open or close independently of the first cover of the first compartment, a display attached to the first cover and the second cover allowing the first cover to open or close independently of the second cover, and processing circuitry configured to transmit an alert signal to the display when the first dose time is reached.

12 Claims, 12 Drawing Sheets

(51) Int. Cl.
*A61B 5/00* (2006.01)
*A61B 5/145* (2006.01)

(56) References Cited

U.S. PATENT DOCUMENTS

| | | | | |
|---|---|---|---|---|
| 5,915,558 | A * | 6/1999 | Girvetz | A61J 7/0481 |
| | | | | 206/534 |
| 6,340,242 | B1 * | 1/2002 | Sandidge | G04B 37/127 |
| | | | | 368/223 |
| 6,464,389 | B1 * | 10/2002 | Ghoorahoo | A61J 7/0481 |
| | | | | 368/223 |
| 2006/0018200 | A1 * | 1/2006 | Pitocco | G04G 11/00 |
| | | | | 368/223 |
| 2009/0086579 | A1 * | 4/2009 | Clark | A47G 29/1209 |
| | | | | 368/10 |
| 2015/0174005 | A1 | 6/2015 | Piering | |

OTHER PUBLICATIONS forgettingthepill.com, "Beatfirst—Pill Holder Bracelet—Items 305 & 306", Wayback Machine Internet Archive, URL: http://www.pillthing.com/products/beatfirst-pill-holder-bracelet, 4 Pages total, (Oct. 28, 2014).

* cited by examiner

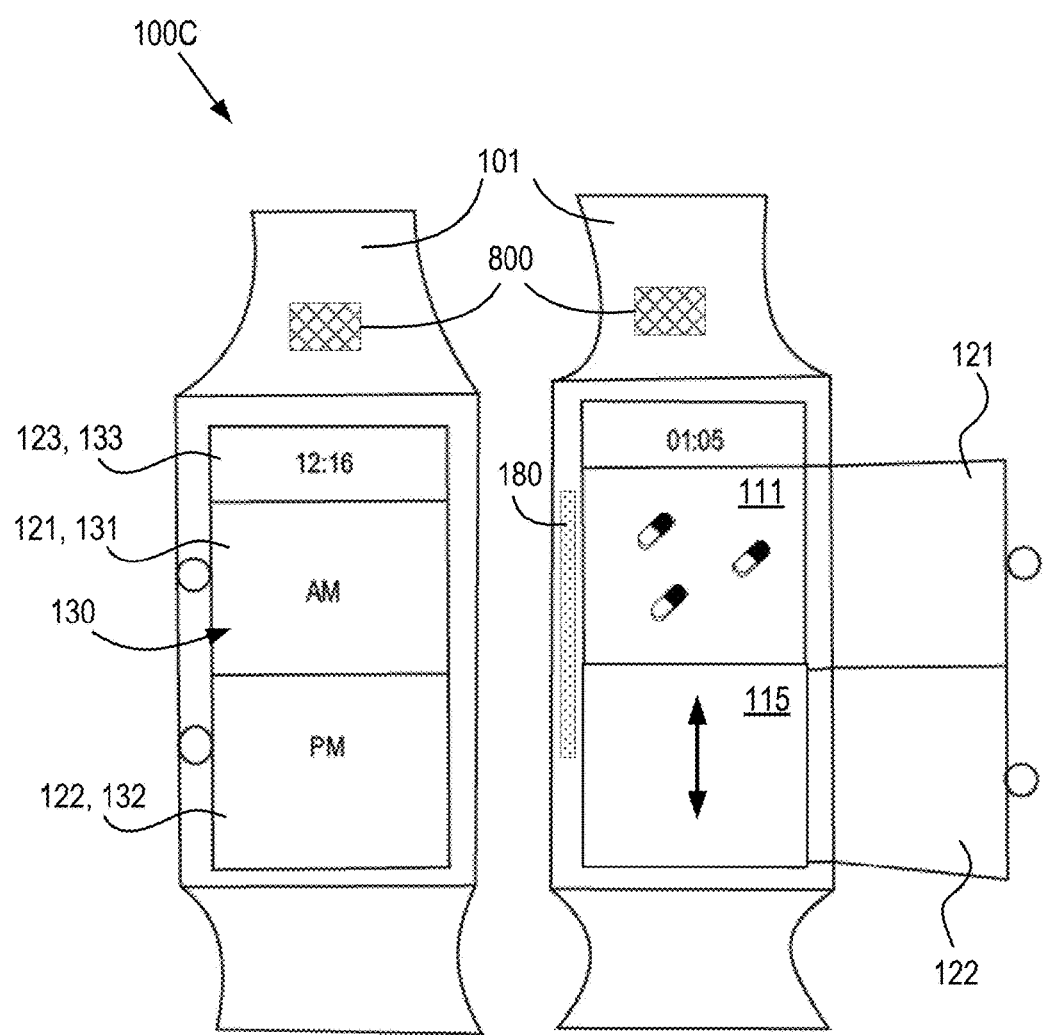
FIG. 1C  FIG. 1D

WEARABLE PILLBOX REMINDER

GRANT OF NON-EXCLUSIVE RIGHT

This application was prepared with financial support from the Saudi Arabian Cultural Mission, and in consideration therefore the present inventor(s) has granted The Kingdom of Saudi Arabia a non-exclusive right to practice the present invention.

BACKGROUND

Oftentimes, patients may have chronic medical conditions which may require patients to take medication on regular basis to get better, or to prevent the condition from getting worse. For such patients, a pillbox having several containers is designed to organize and store the medication.

The pillbox can include more than one container, for example, seven containers, one for each day of the week. Furthermore, each container of the pillbox can be labelled and/or color coded to indicate a particular day such as Monday, Tuesday, and so on. Each container can store medicine (also referred as a dose, pills or medication) to be consumed on a particular day. Such a pillbox can be stored away in a medical cabinet at home or carried in a bag/purse. However, the patient must remember to take the medication each day at a particular time. Missing a dose on a regular basis may be harmful for the patient. As such, there remains a continuing need to provide an improved pillbox that can store and alert user to take medication on time.

SUMMARY

According to an embodiment of the present disclosure, there is provided a wearable pillbox apparatus. The apparatus includes a first compartment hingedly connected with a first cover and configured to store medicine to be consumed at a first dose time, a second compartment hingedly connected with a second cover and configured to store medicine to be consumed at a second dose time, the second compartment located adjacent to the first compartment and the second cover configured to open or close independently of the first cover of the first compartment, a display attached to the first cover and the second cover allowing the first cover to open or close independently of the second cover, and processing circuitry. The processing circuitry is configured to receive the first dose time and the second dose time, transmit an alert signal to the display when the first dose time is reached, detect, while the alert signal is activated, an opening of the first cover and consumption of medicine from the first compartment, and deactivate the alert signal at the display, after the medicine from the first compartment are consumed.

Further, according to an embodiment of the present disclosure, there is provided a wearable pillbox apparatus. The apparatus includes a first compartment configured to store medicine to be consumed at a first dose time, a second compartment configured to store medicine to be consumed at a second dose time, the second compartment located adjacent to the first compartment, a cover hingedly connected over the first compartment and the second compartment, a display attached to the cover having a first portion and a second portion, the first portion of the display configured to receive an alert signal related to the first compartment and the second portion of the display configured to receive an alert signal related to the second compartment, and processing circuitry. The processing circuitry configured to receive the first dose time and the second dose time, transmit an alert signal to the first portion of the display when the first dose time is reached, detect, while the alert signal is activated, an opening of the cover and consumption of medicine from the first compartment, and deactivate the alert signal at the display, after the medicine from the first compartment are consumed.

Further, according to an embodiment of the present disclosure, there is provided a method for reminding to take a dose. The method includes receiving, via processing circuitry, a first dose time and a second dose time, transmitting, via a network, an alert signal to a display of a pillbox when the first dose time is reached, in response to the alert signal, detecting, via the processing circuitry, an opening of the first cover and consumption of one or more medicine from a first compartment, and deactivate the alert signal at the display, after the one or more medicine from the first compartment is consumed.

The forgoing general description of the illustrative implementations and the following detailed description thereof are merely exemplary aspects of the teachings of this disclosure, and are not restrictive.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 1C illustrates a first variation of the wearable pillbox in a close state according to an exemplary embodiment of the present disclosure;

FIG. 1D illustrates the wearable pillbox of FIG. 1C in an open state according to an exemplary embodiment of the present disclosure;

DETAILED DESCRIPTION

Figures 1A, 1B:
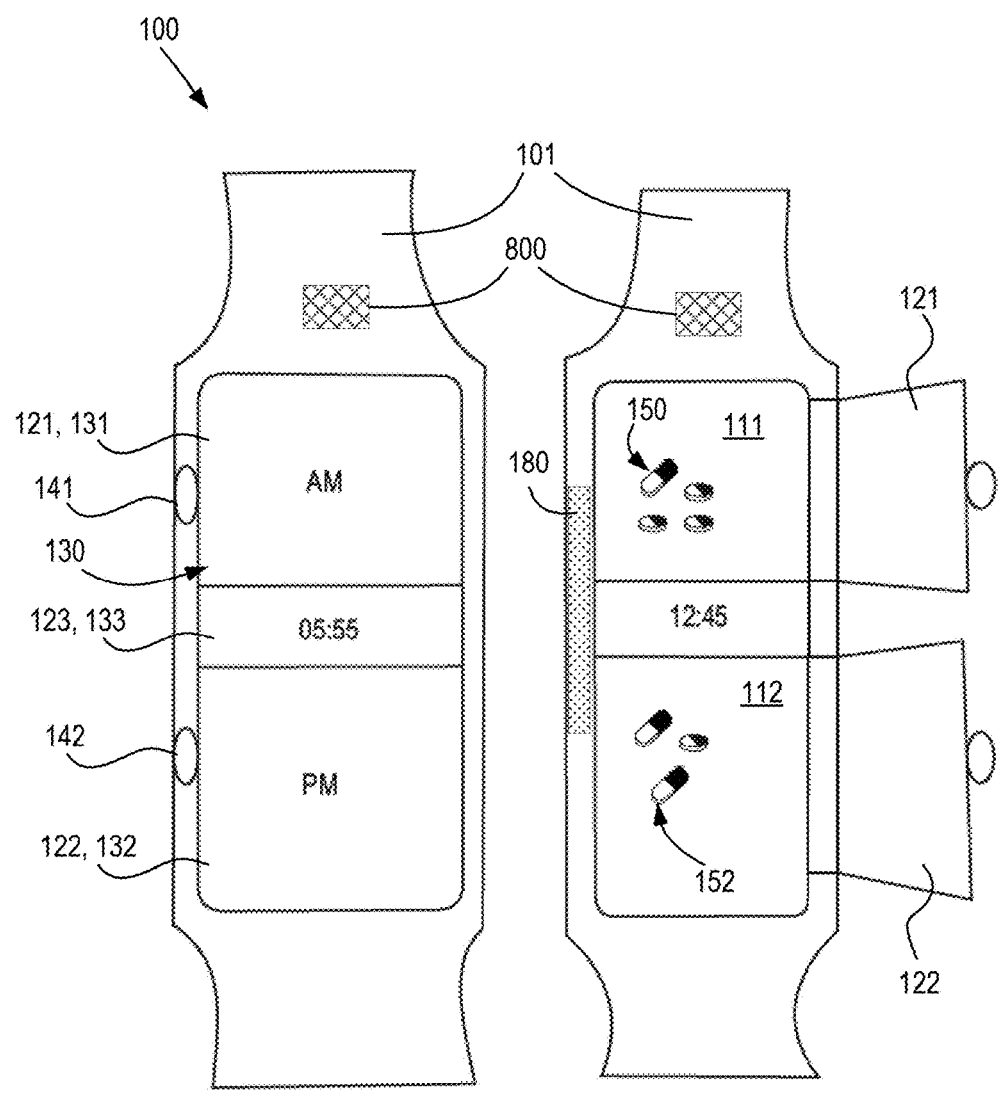
FIG. 1A illustrates a wearable pillbox in a close state according to an exemplary embodiment of the present disclosure.
FIG. 1B illustrates the wearable pillbox in an open state according to an exemplary embodiment of the present disclosure.

The description set forth below in connection with the appended drawings is intended as a description of various embodiments of the disclosed subject matter and is not necessarily intended to represent the only embodiment(s). In certain instances, the description includes specific details for the purpose of providing an understanding of the disclosed embodiment(s). However, it will be apparent to those skilled in the art that the disclosed embodiment(s) may be practiced without those specific details. In some instances, well-known structures and components may be shown in block diagram form in order to avoid obscuring the concepts of the disclosed subject matter.

Reference throughout the specification to "one embodiment" or "an embodiment" means that a particular feature, structure, or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "top," "bottom," "side," and the like that may be used herein merely describe points of reference and do not necessarily limit embodiments of the present disclosure to any particular orientation or configuration.

Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

A patient with chronic medical conditions such as diabetes, heart disease, high blood pressure, etc. may take medication (or prescribed dose) on regular basis. Such patient has to remember to take the medication each day at a particular time. However, often times, the patient forgets to take the medication on time and/or may skip a dose for the day. Such situation may arise due to memory problems with the patient, no caretaker, the patient is on travel, or other situations where the patient may not access to the medication on time.

For such patent, missing a dose may be harmful for the patient. As such, there remains a continuing need to provide an improved pillbox that the patient (or other user e.g., a patient's caretaker or parents of a kid with medical condition) can carry with him/her, the pillbox can be readily accessible, and can alert the patient to take the dose on time.

In the present disclosure, medicine can refer to medication or other substances that must be consumed on a regular basis at a particular time of a day.

FIGS. 1A and 1B illustrate a wearable pillbox 100 in a close state and an open state, respectively, according to an exemplary embodiment of the present disclosure. The wearable pillbox 100 includes a band 101, a first compartment 111, a second compartment 112, a first cover 121, a second cover 122, a display 130 (also referred as a display screen), and a reminder controller 800. The first compartment 111 and the second compartment 112 can be separated by a partition 123.

The pillbox 100 can also include one or more sensors 180 such as a proximity sensor configured to detect the proximity of a user, opening or closing of the first cover 121 and/or the second cover 122, a temperature sensor configured to measure a temperature of the pillbox 100, a weight sensor configured to measure a weight within the compartments 111 and/or 112 or other similar sensors. The sensors 180 can be further configured to communicate with the reminder controller 800 so that the reminder controller 800 can determine, based on data received from the sensor 180, whether the first compartment 111 and/or the second compartment 112 was opened or closed, and whether medicine within the compartment were consumed, at what time medicine were consumed and other tracking or reminder functions. As such, the reminder controller 800 can track a timely consumption of medicine. In some implementations, the reminder controller 800 can be located on the band 101, within a compartment (e.g., the first compartment 111 or the second 112), or the cover (e.g., the first cover 121 or the second cover 122). A flowchart of processes performed by the reminder controller 800 is further explained with respect to FIG. 7.

The first compartment 111 and the second compartment 112 are configured to store one or more medicine 150 and 152 (referred to as medicine 150 hereinafter) and can be integrally formed within the band 101. The band 101 can be wrapped around a wrist, an arm or other body part, so that a user can readily access the medicine 150 stored within the first compartment 111 and/or the second compartment 112. The first compartment 111 and the second compartment 112 (collectively referred as compartments 111 and 112 hereinafter) can coated with or made of thermally insulating material to prevent heat from reaching the medicine 150. In addition, the compartments 111 and 112 include a pocket filled with a cooling gel, for example, on a side touching the body part, to keep the medicine within the compartments cool. The medicine 150 and 152 can be the same or different types. For example, medicine 150 and 152 can be for diabetes expected to be consumed at a first dose time (e.g., at 11 am) and a second dose time (e.g., at 6 pm). In another example, the medicine 150 can be different from the medicine 152. For example, the medicine 150 can be for diabetes expected to be consumed at a first dose time (e.g., at 11 am) and the medicine 152 can be for blood pressure expected to be consumed at a second dose time (e.g., at 3 pm).

In FIG. 1A, the compartments 111 and 112 are covered by the first cover 121 and the second cover 122 (also collectively referred as the covers 121 and 122. Furthermore, the display 130 can be attached to the covers 121 and 122. The display 130 can be configured to split the screen of the display 130 in one or more portions such as a first portion 131 can be attached to the first cover 121 and a second portion 132 can be attached to the second cover 122. Furthermore, within the first portion 131, a marker indicating the first dose can be marked. For example, a marker "AM" indicating the first dose (medicine 150) to be taken in the morning from the first compartment 111, and a marker "PM" indicating the second dose (medicine 152) to be taken in the evening form the second compartment 112. Furthermore, the display 130 can include a third portion 133 attached to the partition 123 indicating a time of the day (e.g., 5:55 pm). The first portion 131 and the second portion 132 can be configured to flash light when an alert signal is received from the reminder controller 800. For example, a flashing of the first portion 131 indicates it's time to take the first dose (medicine 150) from the first compartment 111, and a flashing of the second portion 132 indicates it's time to take the second dose (medicine 152) from the second compartment 112. An alert signal can be in a visual, tactical, vibratory, auditory, or other similar forms generated based on the signal received from the reminder controller 800 when a first dose time (i.e., a time at which a first dose should be consumed) or a second dose time (i.e., a time at which a second dose should be consumed) is reached.

The present disclosure is not limited to above configuration of the display. It can be appreciated by a person skilled in the art that the display 130 can be configured differently, for example, as shown in FIGS. 1C, 2A, 2E, 3, 4A, 5A.

The first compartment 111 is hingedly connected with the first cover 121. The first cover 121 can be in a closed state (as shown in FIG. 1A) and locked to the band 101 to prevent access to or prevent spilling of the medicine 150 from the first compartment 111. The first cover 121 can be unlocked from the band 101 and opened using a lip 141 to access the medicine 150 in the compartment 111, as shown in FIG. 1B. The user may open the first cover 121 when the reminder controller 800 sends the alert signal (e.g., a visual flashing light) to the first portion 131 of the display 130. Furthermore, the sensor 180 can detect the opening/closing of the first cover 121, a weight of the first compartment 111, and send a feedback to the reminder controller 800 that the first dose was consumed. The second compartment 112 can be configured in a similar as the first compartment 111, as discussed above. The lips 141 and 142 facilitate opening and closing of the covers 121 and 122, respectively.

One or more parts of the pillbox 100 can be made of a combination of an elastic material such as rubber or plastic, metal such as steel, silver, or gold, or other commonly used materials for wearable devices. For example, the band 101 can be made of flexible rubber, the compartment 111 and 112 can be made of silver, the covers 121 and 122 can be made of plastic, etc. In another implementation, the band 101 and the compartments 111 and 112 can be made of gold to serve as an accessory like a bracelet.

In some implementation, as illustrated in FIGS. 1D and 1C, a wearable pillbox 100C, which is a first variation of the wearable pillbox 100, can include a different configuration of the display 130 and a different access to the compartments 111 and 112. In FIG. 1C, the pillbox 100C can include the first compartment 111 and second compartment 112 adjacent to each other and the partition 123 can be above the first compartment 111. Accordingly, the display 130 can be configured to include the first portion 131 over the first compartment 111, the second portion 132 over the second compartment 112, and the third portion 133 attached to the partition 123. Thus, the current time (e.g., 12:16 pm) can be displayed at a top end. In addition, including the partition 123 above the first compartment 111 (or below the second compartment 112) can allow a seamless connection between the compartments 111 and 112, enabling addition of a slidable panel 115 (in FIG. 1D).

In FIG. 1D, the second compartment. 112 can be covered with a slidable panel 115 configured to slide back and forth between the compartments 111 and 112. The slidable panel 115 can prevent access to or spilling of the medicine 152 in the second compartment 112, particularly, when both covers 121 and 122 are opened and the user is expected (upon alert signal from the reminder controller 800) to consume the first dose (medicine 150) from the first compartment 111. On the other hand, when the user s expected to consume the second dose (medicine 152) from the second compartment 112, the sliding panel 115 can be moved over the first compartment 111, thus allowing access to the medicine in the second compartment 112 and preventing access to the medicine in the first compartment 111. The sliding panel 115 can also be used when the pillbox 100 is configured to include one cover, as illustrated in FIGS. 2A-2F, instead of two covers.

Figures 2C, 2D:
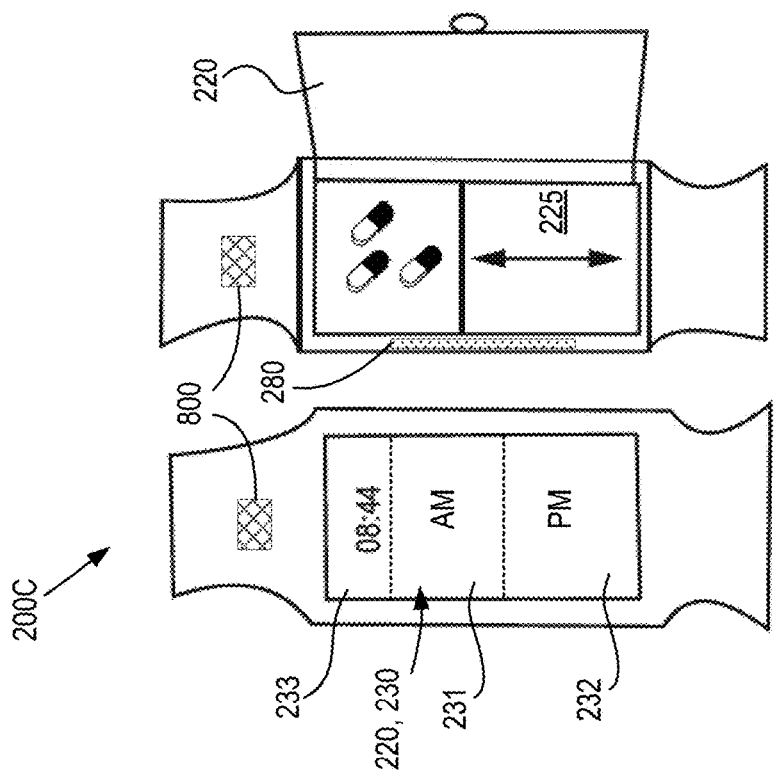
FIG. 2C illustrates a first variation of the wearable pillbox of FIG. 2A in a close state according to an exemplary embodiment of the present disclosure.
FIG. 2D illustrates the wearable pillbox of FIG. 2A in an open state according to an exemplary embodiment of the present disclosure.
Figures 2A, 2B:
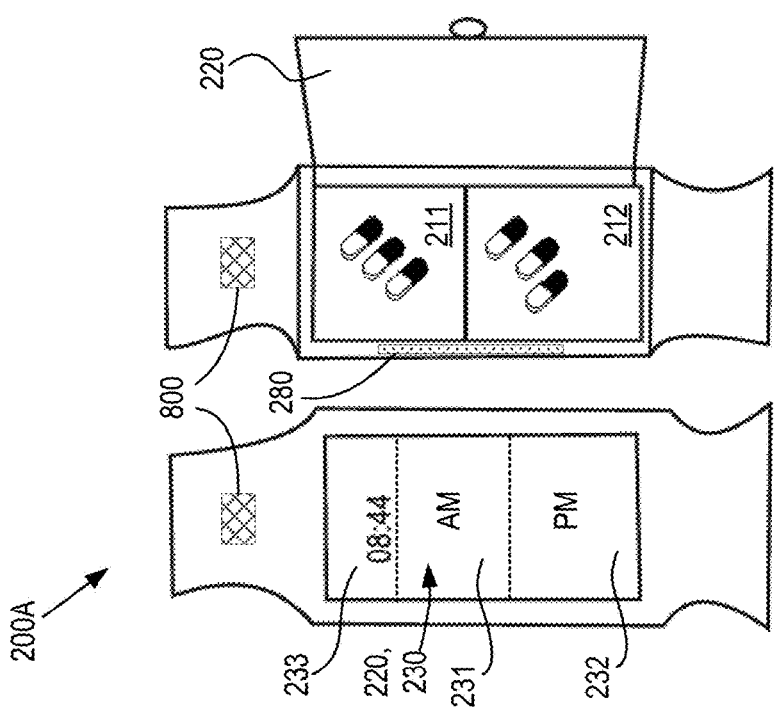
FIG. 2A illustrates a wearable pillbox with one cover in a close state according to an exemplary embodiment of the present disclosure.
FIG. 2B illustrates the wearable pillbox of FIG. 2A in an open state according to an exemplary embodiment of the present disclosure.
Figures 2E, 2F:
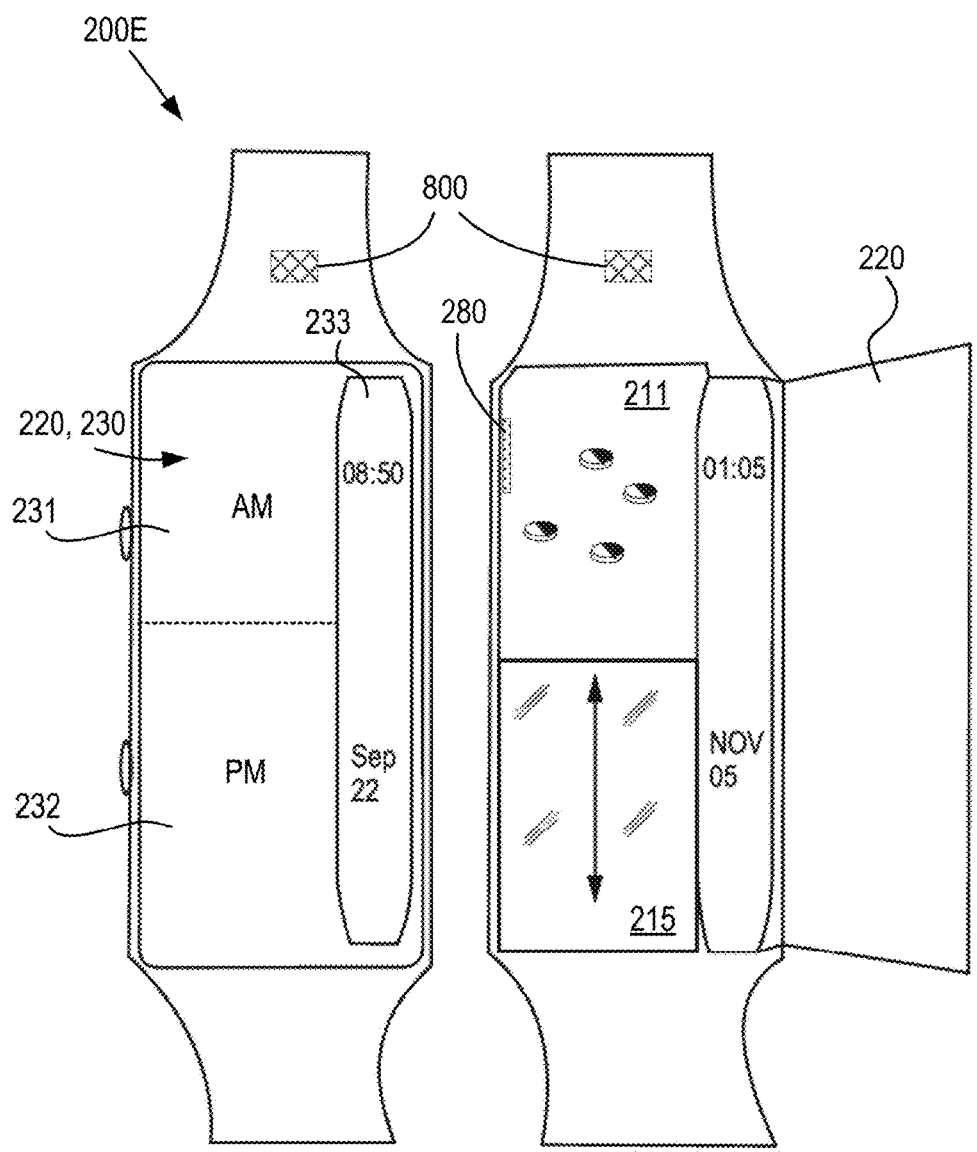
FIG. 2E illustrates a second variation of the wearable pillbox of FIG. 2A in a close state according to an exemplary embodiment of the present disclosure.
FIG. 2F illustrates the wearable pillbox of 2A in an open state according to an exemplary embodiment of the present disclosure.

FIG. 2A illustrates a wearable pillbox 200A with one cover, which is a slightly different implementation of the pillbox 100 and 100C. The pillbox 200A includes a cover 220 covering both the compartments 211 and 222, which are an implementation of the compartments 111 and 112. In some implementations, the compartments 211 and 212 can be separated by a partition 223, but may not include a sliding panel, as illustrated in FIG. 2B. As such, when the cover 220 is opened medicine from both the compartments 211 and 212 are accessible. In some implementations, as illustrated in FIGS. 2D and 2E, a pillbox 200C or 200E (which are variations of pillbox 200A) can include a sliding panel 215, an implementation of the sliding panel 115. Accordingly, when the cover 220 is opened, the sliding panel 215 can be moved back and forth between the compartments 211 and 212 allowing access to either the first compartment 211 or the second compartment 212 at a time. For example, when the second dose is expected to be consumed, based on the alert signal from the reminder controller 800, the sliding panel 215 can be moved over the first compartment 211.

The cover 220 is also attached with a display 230, which includes a continuous screen since there is only one cover, as opposed to the split screens of the display 130 (in FIGS. 1A-1D). As shown in FIGS. 2A, 2C, and 2E, the display 230 can be configured to include a first portion 231 indicating a first marker (e.g., AM) for the first dose, a second portion 232 indicating a second marker (PM) for the second dose, and a third portion 233 to display a current time and/or date.

Figure 3:
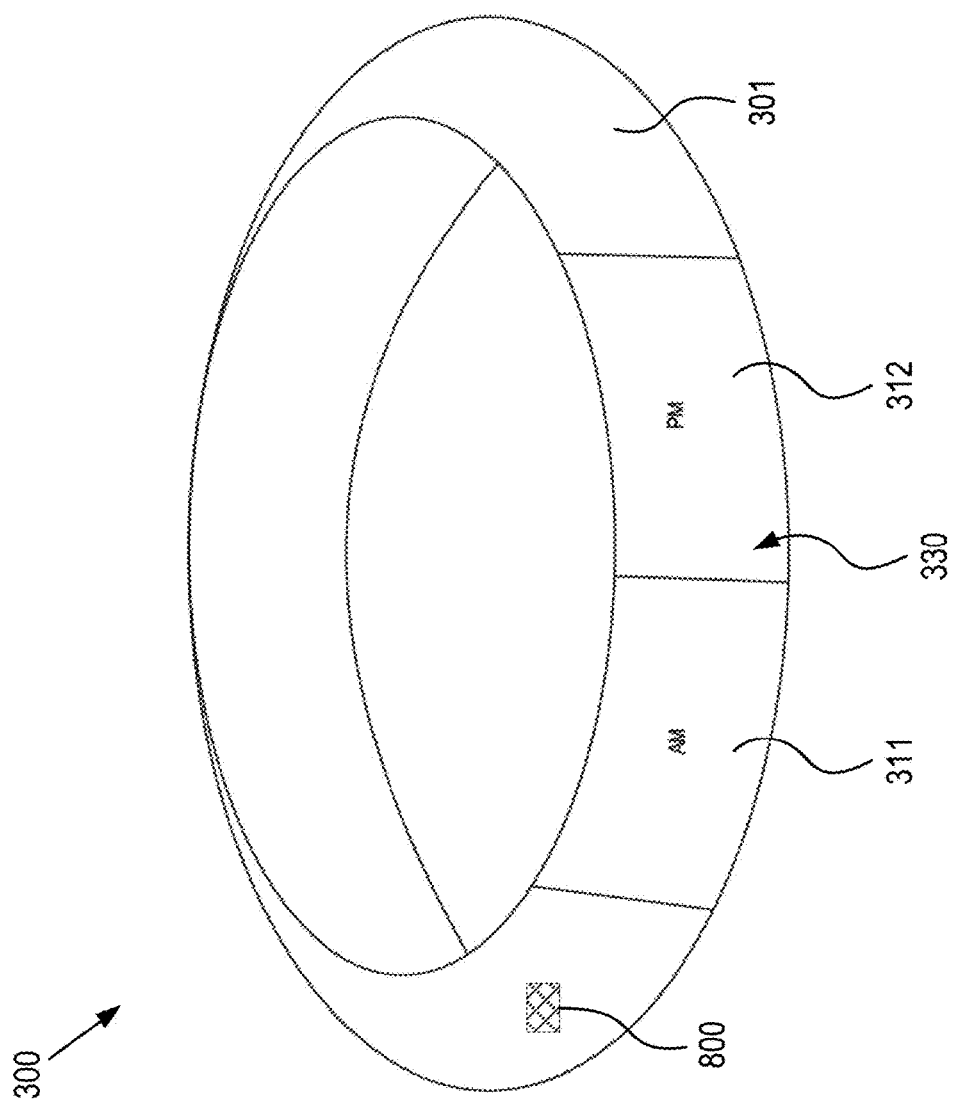
FIG. 3 illustrates a wearable pillbox in a bracelet form according to an exemplary embodiment of the present disclosure.

FIG. 3 illustrates a wearable pillbox 300 in bracelet form according to an exemplary embodiment of the present disclosure. The pillbox 300 includes a bracelet 301 having compartments 311 and 312 with a display 330 indicating the first dose marking (AM) and the second dose marking (PM). The pillbox 300 can also include the reminder controller 800 configured to send alert signal to the display 330. The operation of the pillbox 300 can be similar to that of the pillbox 100, discussed earlier.

Figure 4A:
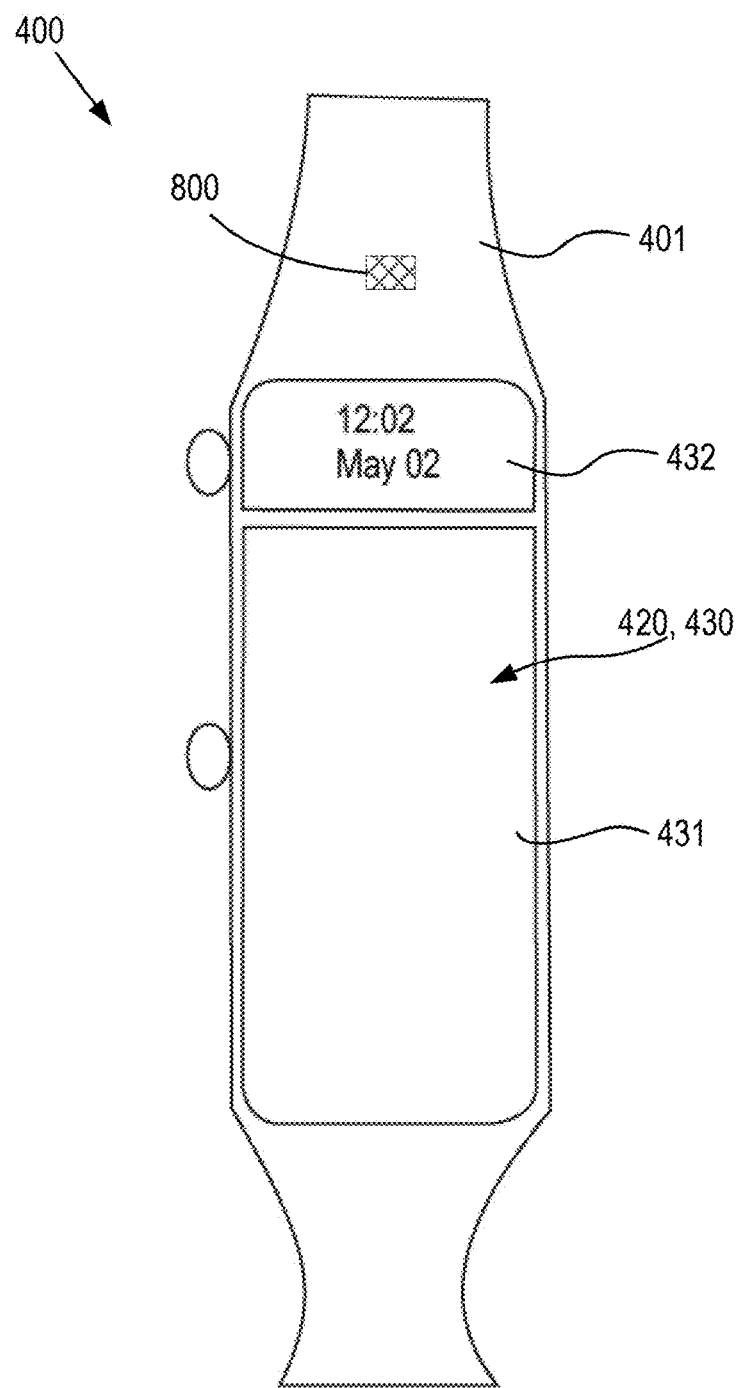
FIG. 4A illustrates a wearable pillbox having one compartment and one cover in a close state according to an exemplary embodiment of the present disclosure.
Figure 4C:
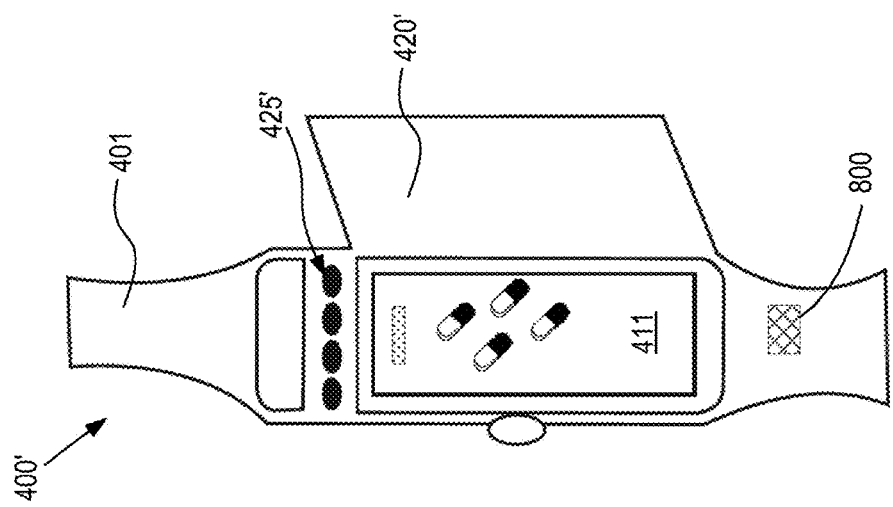
FIG. 4C illustrates a variation of the wearable pillbox of FIG. 4A in an open state according to an exemplary embodiment of the present disclosure.
Figure 4B:
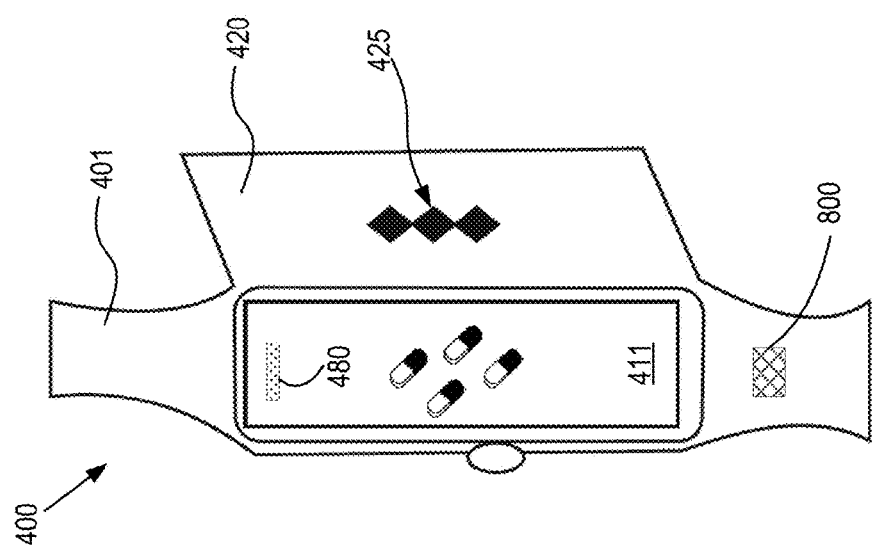
FIG. 4B illustrates the wearable pillbox of FIG. 4A in an open state according to an exemplary embodiment of the present disclosure.

In some implementations, as illustrated in FIGS. 4A, and 4B, a wearable pillbox 400 can include one compartment 411 hinged with one cover 420. The cover 420 can be attached with the display 430. The display 430 can be configured to include a first portion 431, and a time portion 432 that displays time and/or date (e.g., 12:02, and May 2). The first portion 431 of the display 430 can display alert signal received from the reminder controller 800 related to both the first dose and the second dose.

The cover 420 can include the display 430 on a top side, (i.e., side visible when the cover 420 is closed), and an alert device 425 (in FIG. 4B) on a bottom side (i.e., opposite to the top side that is visible when the cover 420 is opened). The display 430 is an implementation of the display 130 and/or 230.

The alert device 425 can be any device configured to receive the alert signal from the reminder controller 800. The alert device 425 can be, for example, the display 130 (or 230, 330, 430, 530), LED lights, vibrator, speaker, or other devices that can be used to alert a user. When the alert device 425 receives the alert signal, the LED lights may light up. Such LED lights can also provide visibility to see medicine in the compartment 411 when it is dark. In some implementation, the alert device 425 can be a vibrator that vibrates in response to the alert signal indicating that the first dose or the second dose time is reached. In some implementation, the alert device 425 can be a speaker that receives the alert signal in audio form from the reminder controller 800.

In some implementations, the alert device 425 can be located at a different location on the pillbox 400 (or pillbox 100, 100C, 200A, etc.). For example, in FIG. 4C, a pillbox 400' includes an alert device 425', which is an implementation of the alert device 425, located on a band 401. In some implementations, the cover 420', which is an implementation of the cover 420, may not include any alert device.

The pillbox 400 can be used when the first dose and the second dose are the same and/or easily identifiable so that the doses may not be stored separately in two different compartments, as discussed earlier in the present disclosure.

Figure 5B:
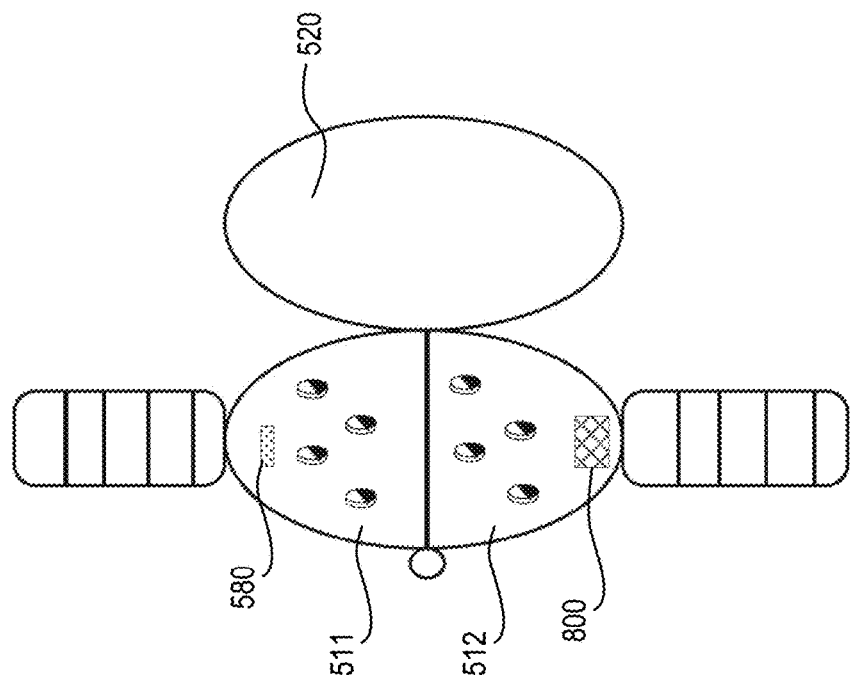
FIG. 5B illustrates the oval shaped wearable pillbox in an open state according to an exemplary embodiment of the present disclosure.
Figure 5A:
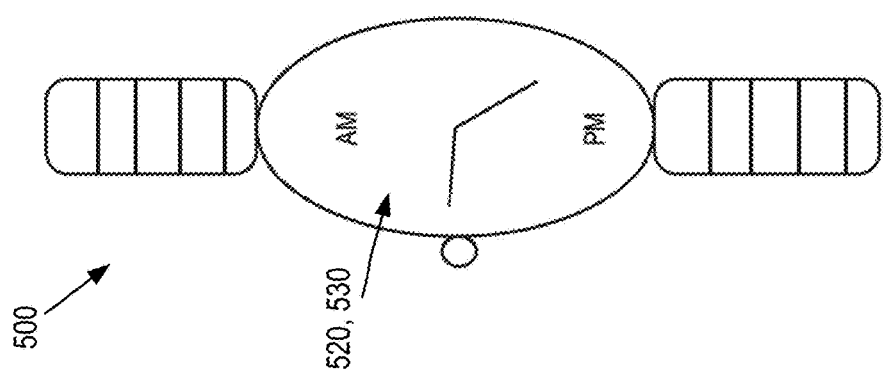
FIG. 5A illustrates a oval shaped wearable pillbox in a close state according to an exemplary embodiment of the present disclosure.

In some implementations, the pillbox can have a rectangular shape, an oval shape, or other geometric shapes desired by a user. For example, FIGS. 5A and 5B illustrate an oval shaped pillbox 500 in a close state and an open state, respectively. In FIGS. 5A and 5B, the pillbox 500 can include a first compartment 511, a second compartment 512, a cover 520 and a display 530. The pillbox 500 is an implementation of the pillbox 200A, hence the description is omitted for brevity. It can be understood that the references to the pillbox 100, 100C, 200A, 200E, 400, 500, etc. can be generally referred as pillbox 100, according to the present disclosure.

Figure 6:
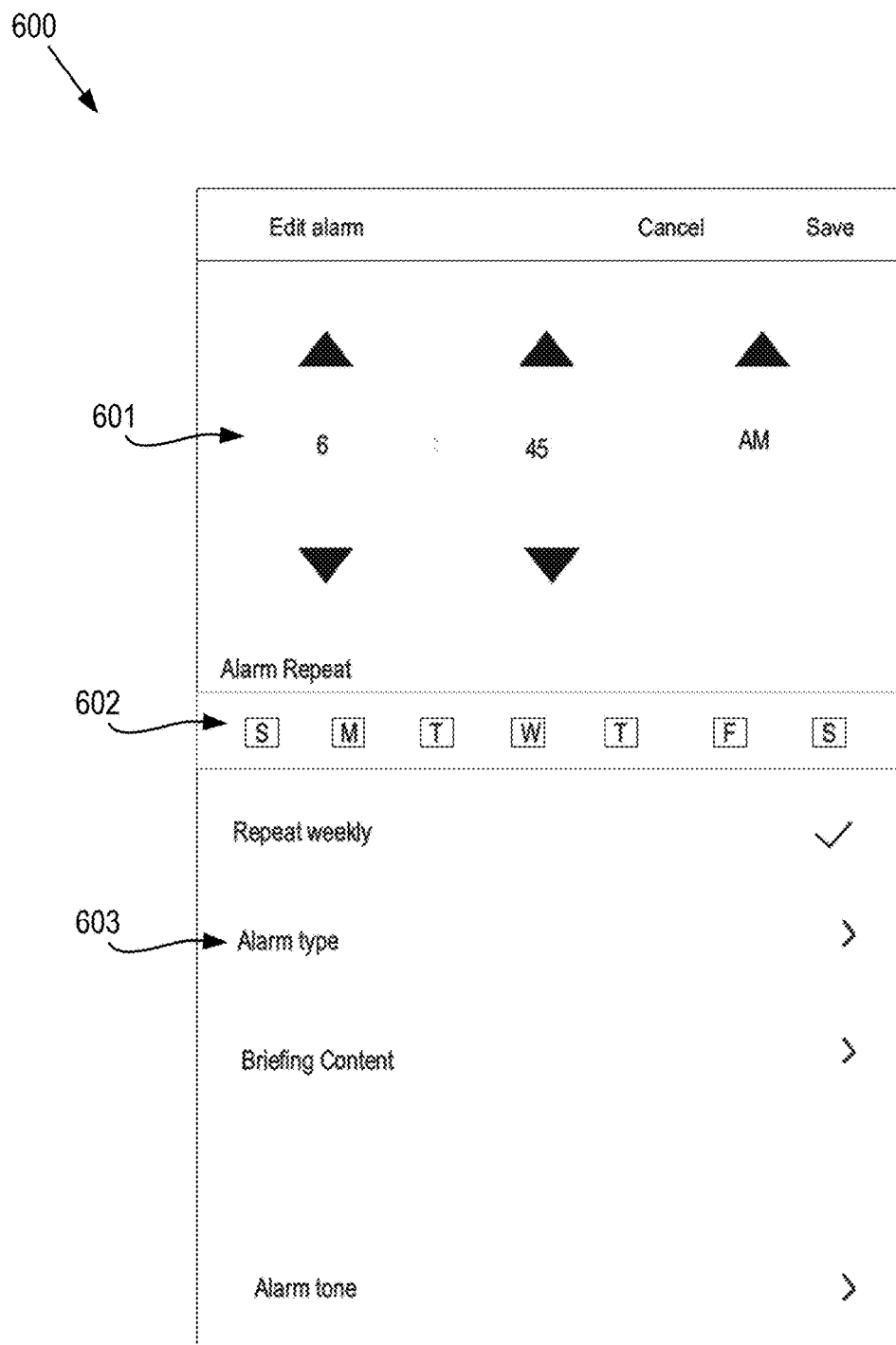
FIG. 6 is a user device used to set an alarm/alert for a wearable pillbox according to an exemplary embodiment of the present disclosure.

FIG. 6 is an alarm interface 600 of a user device 900 (illustrated in FIG. 9) that can be used to set an alarm/alert for the reminder controller 900. Alternatively or in addition, the reminder controller 900 can be configured to include an alert set function similar to that found in digital watches or other alarm setting devices.

The alarm interface 600 can allow an user to enter one or more dose times 601 such as the first dose time and the second dose time, the days 602 on which the one or more doses is expected to the consumed, an alert type 603 such as vibratory, audio, visual or a combination thereof, and other alarm related functions available within the user device. The alarm information can be saved and transmitted to the controller 800, via a network. The controller 800 can further perform a process implemented in circuitry of the controller 800, as discussed with respect to FIG. 7.

Figure 7:
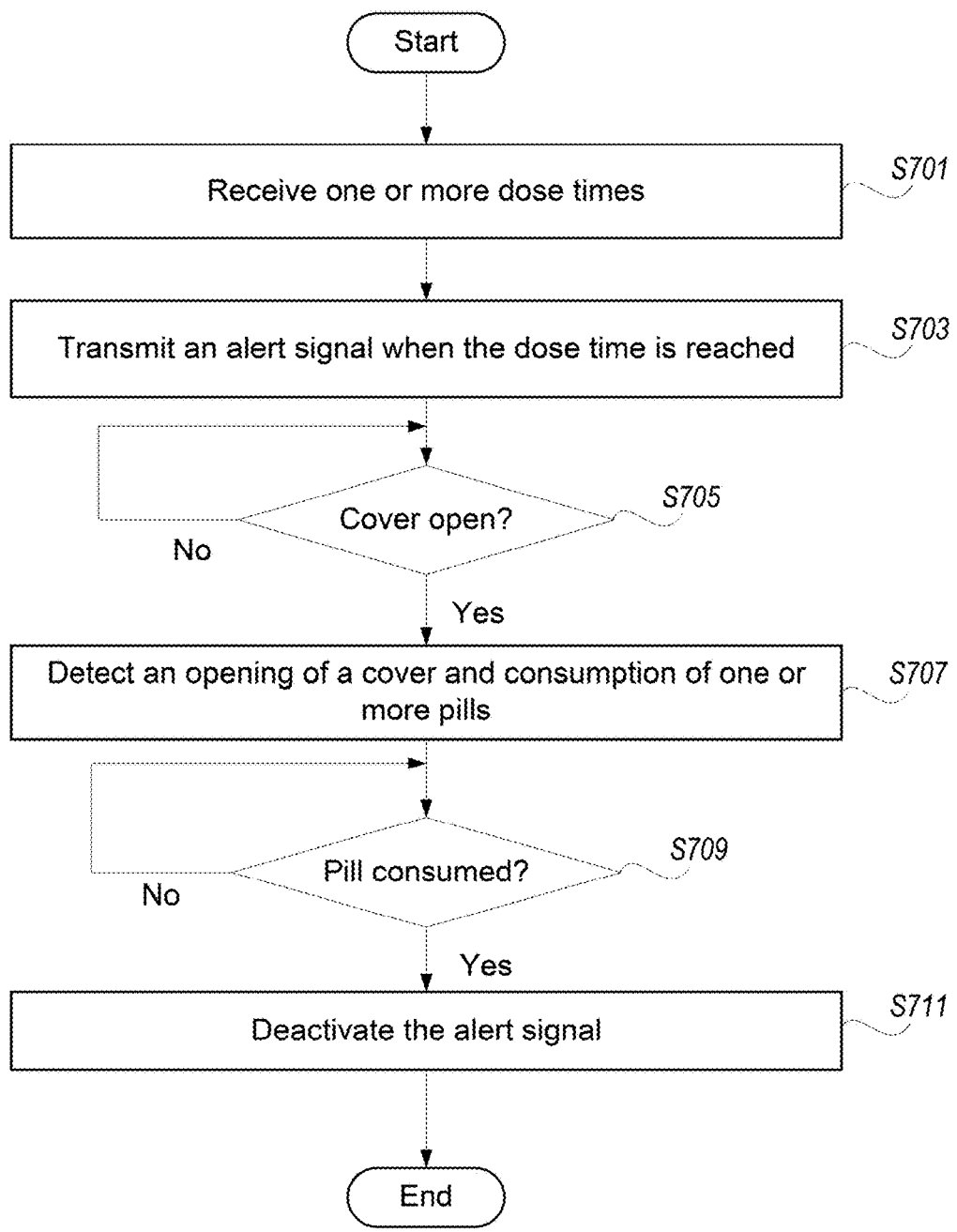
FIG. 7 is a flow chart for a reminder controller of a wearable pillbox according to an exemplary embodiment of the present disclosure.

FIG. 7 is a flow chart for the reminder controller 800 of a wearable pillbox according to an exemplary embodiment of the present disclosure. The process starts when medicine is stored in the pillbox 100.

In step S701, the controller 800 can receive one or more dose times, for example, from a user device 900 via the alarm interface 600 (in FIG. 6). Alternatively, the controller 800 can be configured to receive dose times via the display 130. The dose time indicates a time (e.g., 11 am) at which a dose (i.e., medicine) must be consumed. More than one dose times indicate that multiple doses are expected to be consumed during a day at a particular time of the day. The dose times can be stored in the memory of the controller 800.

When a dose time is reached, in step S703, the controller 800 can transmit an alert signal to the display 130 or the alert device 425 of the pillbox 100. For example, the first dose time can be 11 am, at which time, the controller 800 can send alert signal to the display 130 to start flashing light and/or signal the alert device 425 to vibrate or sound an alarm.

In response to the alert signal, the controller 800, in step S705, determines whether a cover (e.g., the first cover 121, the second cover 122, etc.) was opened. If the cover was not opened, the controller 800 keeps transmitting the alert signal. If the cover is opened, the controller performs step S707.

In step S707, the controller 800 can detect an opening of the cover based on signal received from the sensor 180. The sensor 180 can also measure and transmit a weight of the pillbox 100 which can be used by the controller 800 to determine whether a pill was consumed. Based on a frequency and time of the opening (and closing) of the cover the controller 800 can further determine if a dose was missed, miss-timed, or other diagnostic factors. Such diagnostic factors can be used to track and predict the health condition of the person wearing the pillbox 100.

In step S709, the controller 800 can determine whether a pill (e.g., medicine 150 in the first compartment 111) was consumed based on a signal received from the sensor 180. The sensor 180 can measure, for example, a weight of the pillbox 100. Based on the weight, the controller 800 can determine whether the weight of the pillbox 100 before opening the cover is more than the weight of the pillbox 100 after opening the cover. If the weight reduces after opening the cover (e.g., cover 121), the controller 800 determines the pill is consumed. If the pill is not consumed, the controller 800 keeps transmitting the alert signal to the display 130 or the alert device 425.

When the pill is consumed, in step S711, the controller 800 sends a signal to deactivate the alert signal. Thus, the display 130 can stop flashing or the alert device 425 can stop vibrating.

Each of the functions of the described embodiments may be implemented by one or more processing circuits. A processing circuit includes a programmed processor (for example, a CPU 801), as a processor includes circuitry. A processing circuit may also include devices such as an application specific integrated circuit (ASIC) and conventional circuit components arranged to perform the recited functions.

Figure 8:
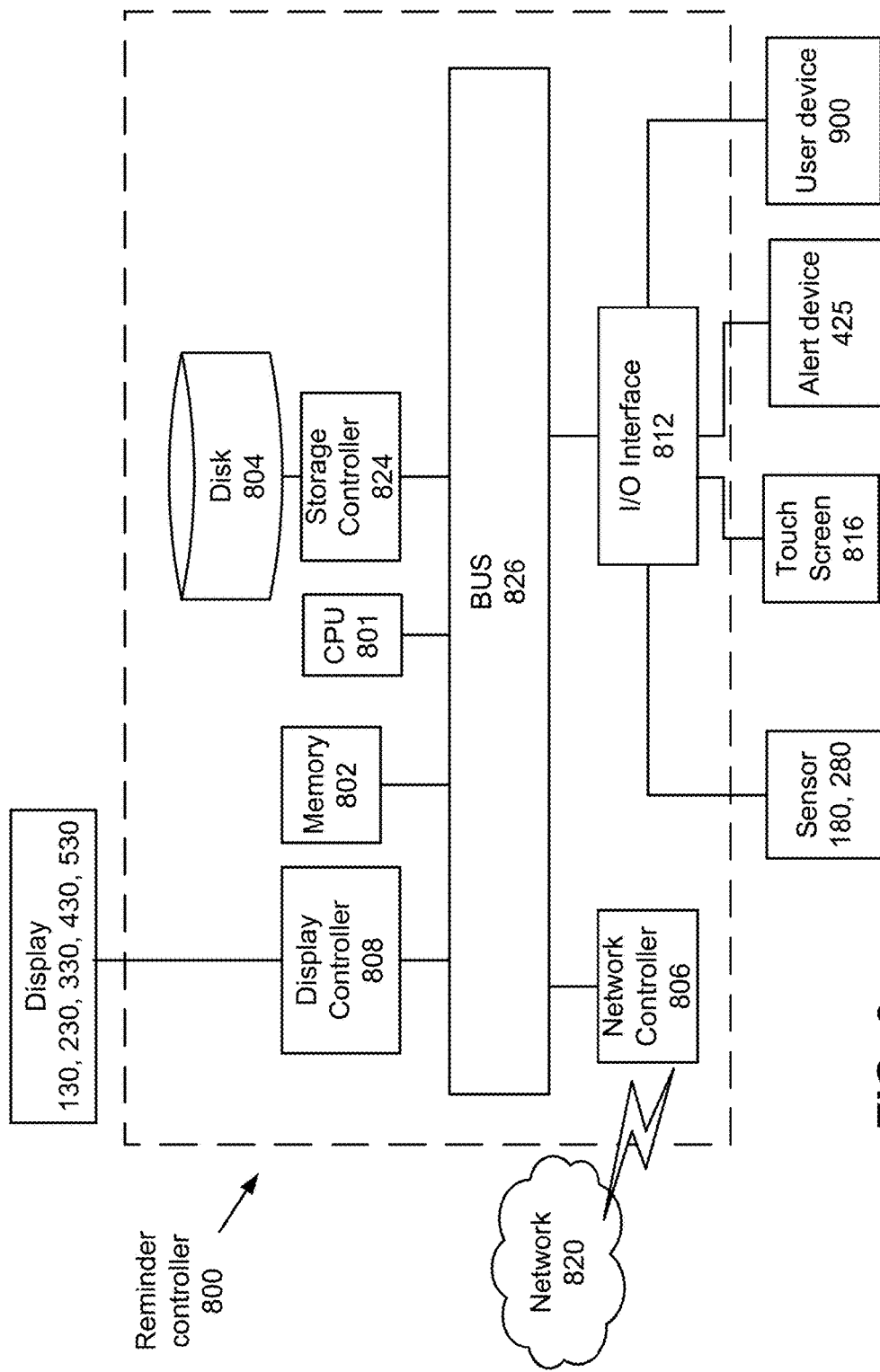
FIG. 8 is a block diagram illustrating the reminder controller according to an exemplary embodiment of the present disclosure.

FIG. 8 is a block diagram illustrating the reminder controller 800 according to an exemplary embodiment of the present disclosure. In FIG. 8, the reminder controller 800 includes a CPU 801 which can be configured to receive inputs from one or more sensors 180 and 280, the user device 900, process the data received to transmit an alert signal to activate the alert device 425 and/or the display 130, 230, 330, 430, 530, and 630. The process data and instructions may be stored in the memory 802. The reminder controller 800 can receive one or more dose times such as the first dose time and the second dose time, generate an alert signal when the dose time is reached and transmit the alert signal to the display 130 and/or the alert device 425. Thus, alerting a user to take the medicine stored in the first compartment or the second compartment of the pillbox 100. Further, the reminder controller 800 can determine whether medicine was consumed or the dose was missed based on the signal received from the sensors.

The hardware elements, in order to achieve the reminder controller 800, may be realized by various circuitry elements, known to those skilled in the art. For example, CPU 801 may be a XENON or Core processor from INTEL of America or an Opteron processor from AMD of America, or may be other processor types that would be recognized by one of ordinary skill in the art. Alternatively, the CPU 801 may be implemented on an FPGA, ASIC, PLD or using discrete logic circuits, as one of ordinary skill in the art would recognize. Further, CPU 801 may be implemented as multiple processors cooperatively working in parallel to perform the instructions of the processes described above with respect to FIG. 7.

The CPU 801 which performs the processes described in the present disclosure. The process data and instructions may be stored in a memory 802. These processes and instructions (discussed with respect to FIG. 7) may also be stored on a storage medium disk 804 such as a hard drive (HDD) or portable storage medium or may be stored remotely.

The reminder controller 800 further includes a display controller 808, such as a NVIDIA GeForce GTX or Quadro graphics adaptor from NVIDIA Corporation of America for interfacing with display 130. A touch screen panel 816 may be on or separate from display 130.

The reminder controller 800 also includes a network controller 806 for interfacing with a network 820. Such network based interfacing can be useful to send commands, sensor data, or alert signal to an external device such as a server for analyzing the pill consumption data including missed doses, timely consumption based on opening and closing of the covers of the compartments and weight of the compartments, temperature of pillbox, etc.

An I/O interface 812 interfaces with one or more sensor 180 and 280, the alert device 425, user device 900, and a touch screen 816 of the display 130, 230, 330, 430, 530, etc. to send and receive inputs or to send activation/deactivation signals to the display and/or the alert device 425.

The storage controller 824 connects the memory 802 with communication bus 826, which may be an ISA, EISA, VESA, PCI, or similar device, for interconnecting all of the components of the reminder controller 800. A description of the general features and functionality of the storage controller 824, network controller 806, and the I/O interface 812 is omitted herein for brevity as these features are known.

Figure 9:
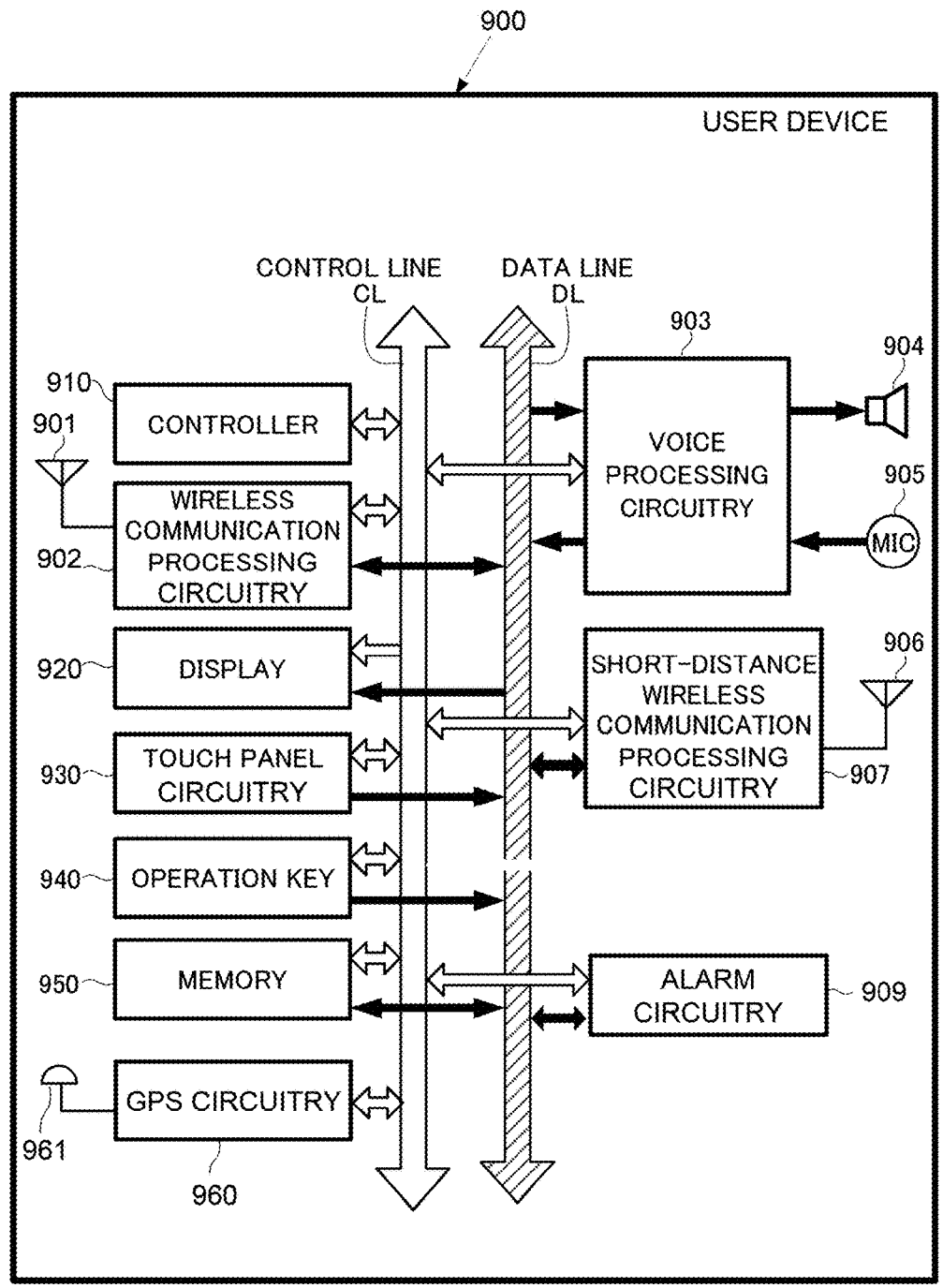
FIG. 9 is a block diagram illustrating a user device according to an exemplary embodiment of the present disclosure.

FIG. 9 is a block diagram illustrating a user device 900 according to an exemplary embodiment of the present disclosure. In certain embodiments, the user device 900 may be a smartphone. However, the skilled artisan will appreciate that the features described herein may be adapted to be implemented on other devices (e.g., a laptop, a tablet, a server, an e-reader, a camera, a navigation device, etc.). The exemplary user device 900 includes a controller 910 and a wireless communication processing circuitry 902 connected to an antenna 901. A speaker 904 and a microphone 905 are connected to a voice processing circuitry 903.

The controller 910 may include one or more Central Processing Units (CPUs), and may control each element in the user device 900 to perform functions related to communication control, audio signal processing, control for the audio signal processing, still and moving image processing and control, and other kinds of signal processing. The controller 910 may perform these functions by executing instructions stored in a memory 950.

The antenna 901 transmits/receives electromagnetic wave signals between base stations for performing radio-based communication, such as the various forms of cellular telephone communication. The wireless communication processing circuitry 902 controls the communication performed between the user device 900 and other external devices such as the reminder controller 800 via the antenna 901. The wireless communication processing circuitry 902 may control communication between base stations for cellular phone communication.

The exemplary user device 900 may also include a display 920, a touch panel 930, an operation key 940, and a short-distance communication processing circuitry 907 connected to an antenna 906. The display 920 may be a Liquid Crystal Display (LCD), an organic electroluminescence display panel, or another display screen technology.

For simplicity, the present disclosure assumes the touch panel 930 is a capacitance-type touch panel technology. However, it should be appreciated that aspects of the present disclosure may easily be applied to other touch panel types (e.g., resistance-type touch panels) with alternate structures. In certain aspects of the present disclosure, the touch panel 930 may include transparent electrode touch sensors arranged in the X-Y direction on the surface of transparent sensor glass.

The antenna 906 may transmit/receive electromagnetic wave signals to/from other external apparatuses, and the short-distance wireless communication processing circuitry 907 may control the wireless communication performed between the other external apparatuses. Bluetooth, IEEE 802.11, and near-field communication (NFC) are non-limiting examples of wireless communication protocols that may be used for inter-device communication via the short-distance wireless communication processing circuitry 907.

The user device 900 may include alarm circuitry 909 configured to provide the interface 600 for entering one or more dose times as discussed with respect to FIG. 6. The alarm circuitry 909 can be configured to transmit the dose times to the reminder controller 800 via the network 820. Also, the user device 900 can receive signal from the sensor 180 and 280 indicating the cover was opened or closed, whether the medicine were consumed, and in response to the medicine consumed, the alarm circuitry 909 can send signal to deactivate the alert signal. Of course such functions can also be performed by the reminder controller 800 as well.

According to one embodiment, the pill box 100 can also include following features compatibility with ANDROID phones, water resistant, Up to 1 month battery usage, tracking steps, distance, calories, and light and restful sleep, anti-lost/finding phone feature (e.g., when Bluetooth is disconnected or the phone is out of the Bluetooth distance) where the a user device (e.g., a watch) can be configured to alert the user when out of range. Furthermore, the pillbox 100 can be configured to send notifications other users (e.g., parents) if the user wearing the pillbox 100 forgets to take pills. The parents or other family members can set the alarm for the pillbox 100 and also store and monitor history log regarding medicine consumption, opening/closing of the pillbox etc. By one embodiment, pillbox 100 can be configured to receive and/or capture an image of medicine and save the image on the user device or controller 800. Furthermore, at the dose time, a notification about the time, name and the picture of medicine to be consumed can be send to the pillbox 100 or the user device so that an incorrect medicine is not consumed.

In the above description, any processes, descriptions or blocks in flowcharts should be understood as representing modules, segments or portions of code which include one or more executable instructions for implementing specific logical functions or steps in the process, and alternate implementations are included within the scope of the exemplary embodiments of the present advancements in which functions can be executed out of order from that shown or discussed, including substantially concurrently or in reverse order, depending upon the functionality involved, as would be understood by those skilled in the art. The various elements, features, and processes described herein may be used independently of one another, or may be combined in various ways. All possible combinations and subcombinations are intended to fall within the scope of this disclosure.

While certain embodiments have been described, these embodiments have been presented by way of example only, and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosure. The accompanying claims and their equivalents are intended to cover such forms or modifications as would fall within the scope and spirit of the present disclosure. For example, this technology may be structured for cloud computing whereby a single function is shared and processed in collaboration among a plurality of apparatuses via a network.

What is claimed is:

1. A wearable pillbox comprising:
    a first compartment hingedly connected with a first cover and configured to store medicine to be consumed at a first dose time;
    a second compartment hingedly connected with a second cover and configured to store medicine to be consumed at a second dose time, the second compartment being located adjacent to the first compartment and the second cover configured to open or close independently of the first cover of the first compartment;
    a first display attached to the first cover and a second display attached to the second cover allowing the first cover to open or close independently of the second cover; and
    processing circuitry configured to
        receive the first dose time and the second dose time,
        transmit an alert signal to the first display when the first dose time is reached,
        detect, while the alert signal is activated, an opening of the first cover and consumption of medicine from the first compartment, and
        deactivate the alert signal at the first display, after the medicine from the first compartment is consumed.

2. The wearable pillbox according to claim 1, wherein the first compartment and the second compartment are thermally insulated to prevent heat from reaching the medicine.

3. The wearable pillbox according to claim 2, wherein the display is configured to display a current time, an AM marking on the first cover, and a PM marking on the second cover.

4. The wearable pillbox according to claim 3, wherein the display is further configured to generate flashing light in response to the alert signal transmitted by the processing circuitry.

5. The wearable pillbox according to claim 4, wherein each of the first cover and the second cover include a lip to facilitate opening and closing of the respective covers.

6. The wearable pillbox according to claim 1, further comprising:
    a slidable panel attached over the second compartment and configured to slide over the first compartment when both the first cover and the second cover are open.

7. The wearable pillbox according to claim 1, further comprising:
    LED lights placed around at least one of the first compartment and the second compartment, wherein the processing circuitry activates the LEDS lights in response to transmitting the alert signal.

8. The wearable pillbox according to claim 1, further comprising:
    a vibrator configured to receive the alert signal from the processing circuitry and generate a vibration signal in response to the alert signal.

9. The wearable pillbox according to claim 1, further comprising:
    a speaker configured to receive the alert signal from the processing circuitry and generate a sound signal in response to the alert signal.

10. The wearable pillbox according to claim 1, further comprising:
    a heart rate sensor configured to measure a heart rate,
    wherein the processing circuitry transmits another alert when the heart rate exceeds an upper heart rate threshold or falls below a lower heart rate threshold.

11. The wearable pillbox according to claim 1, further comprising:
    a glucose level sensor configured to measure a glucose level,
    wherein the processing circuitry transmits another alert when the glucose level falls below a glucose threshold.

12. The wearable pillbox according to claim 1, further comprising:
    a weight sensor configured to measure a weight of the pillbox,
    wherein the processing circuitry determines whether the medicine is consumed by comparing the weight of the pillbox before and after the alert signal is transmitted.

* * * * *